United States Patent [19]

Buell

[11] Patent Number: 4,555,244

[45] Date of Patent: Nov. 26, 1985

[54] WASTE-CONTAINMENT GARMENT HAVING ABSORBENT BODY AND REUSEABLE SIDE-BRIDGING FASTENER FITMENTS

[75] Inventor: Kenneth B. Buell, Cincinnati, Ohio

[73] Assignee: The Procter & Gamble Company, Cincinnati, Ohio

[21] Appl. No.: 517,098

[22] Filed: Jul. 25, 1983

[51] Int. Cl.$^4$ .............................................. A41B 13/02
[52] U.S. Cl. ................................ 604/392; 604/385 A
[58] Field of Search ............... 604/392, 386, 385, 371, 604/398, 401; 128/159; 24/585, 453, 588, 231

[56] References Cited

U.S. PATENT DOCUMENTS

| | | | |
|---|---|---|---|
| 2,119,610 | 6/1938 | Tasker | 604/401 |
| 2,419,867 | 4/1947 | Woodman | 128/159 X |
| 2,471,048 | 5/1949 | Terchick | 604/386 |
| 2,871,592 | 2/1959 | Polzin | 24/585 X |
| 3,771,524 | 11/1973 | Ralph | 604/398 |
| 3,860,003 | 1/1975 | Buell | 604/385 |
| 4,315,508 | 2/1982 | Bolick | 604/371 |

*Primary Examiner*—William H. Grieb
*Attorney, Agent, or Firm*—Thomas J. Slone; Fredrick H. Braun; Richard C. Witte

[57] ABSTRACT

A waste-containment garment comprising a relatively narrow, disposable, absorbent body having elasticized leg cuffs, and reuseable side-bridging fastener fitments for securing the absorbent body on a wearer. The absorbent body comprises an absorbent core and a liquid impervious backsheet. Preferably, it also includes a liquid pervious, hydrophobic topsheet. The absorbent body has waistband regions having total widths of less than the midsection girths of intended users and, preferably, the absorbent core has front and back waistband regions which have individual widths of from about fifteen to about forty-five percent of the midsection girths of intended users or, nominally, about one quarter of the midsection girth of an average size intended wearer. The absorbent body is so elasticized along its longitudinal side edges that, when properly secured on a wearer through the use of the reuseable side-bridging fastener fitments, the elasticized side edges are sufficiently tensioned to form liquid seals or leg cuffs along upper thigh regions of the wearer: particularly, along the inner spans of the upper thigh regions of the wearer. The insert may be provided with reinforcing means such as grommets on its corners to facilitate fastening it with, for example, snap-fastener type fastener fitments.

8 Claims, 7 Drawing Figures

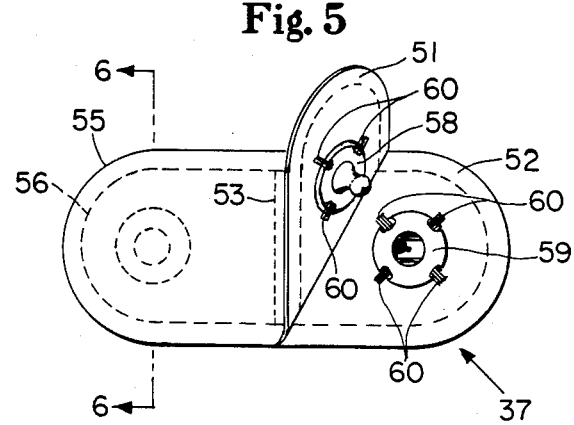
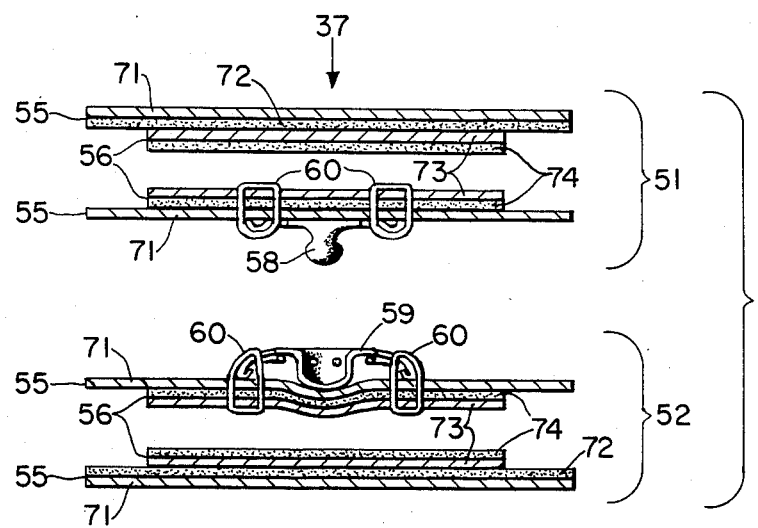
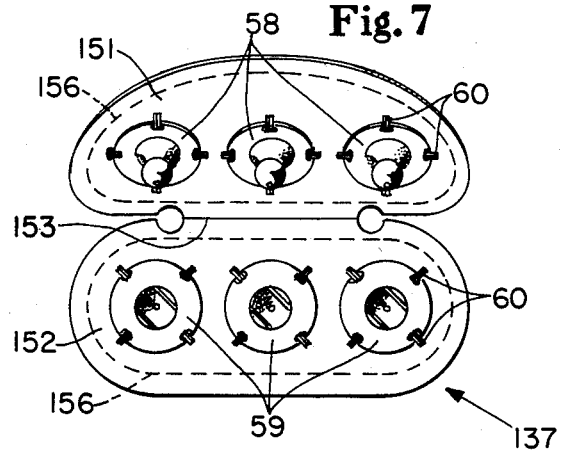

4,555,244

WASTE-CONTAINMENT GARMENT HAVING ABSORBENT BODY AND REUSEABLE SIDE-BRIDGING FASTENER FITMENTS

DESCRIPTION

1. Technical Field

This invention pertains to waste-containment garments such as disposable diapers and means for securing such garments on wearers thereof. More specifically, this invention pertains to such garments comprising disposable absorbent bodies and reuseable side-bridging fastener fitments: e.g., snap-type fastener fitments.

2. Background Art

U.S. Pat. No. 4,315,508 which issued FEB. 16, 1982 to Martha E. Bolick discloses a waste-containment garment comprising a disposable absorbent pad, and reuseable refastenable elastic straps for securing the pad on a wearer. The elastic straps are relatively long, and have high strain and low stress properties so that they angle downwardly from just above the wearer's hip bones to their points of engagement in the corner regions of the absorbent pad.

U.S. Pat. No. 2,419,867 which issued Apr. 29, 1947 to E. Woodman and U.S. Pat. No. 2,471,048 which issued May 24, 1949 to K. A. Terchick disclose reuseable baby garments (e.g., diapers) having short straps which extend laterally from each rear corner of an absorbent body, and which comprise means (e.g., buttons/button holes or snap fasteners) for securing the distal ends of the straps to the front corners of their absorbent pads. The Woodman garment as shown has elasticized longitudinal edges in its crotch region.

U.S. Pat. No. 3,771,524 which issued Nov. 13, 1973 to Harold J. Ralph discloses a diaper garment which comprises a reuseable retainer having a liner secured therein, and which retainer is secured on a wearer through the use of belt-type straps which are stated to preferably be of elastic material. U.S. Pat. No. 2,119,610 which issued June 7, 1938 to R. A. Tasker also discloses a retainer-liner type diaper garment and in some embodiments secures them on a wearer through the use of two side straps and a band which may be discrete elements or a unitary assembly.

U.S. Pat. No. 3,860,003 which issued Jan. 14, 1975 to Kenneth Barclay Buell—the inventor of the present invention—discloses a full-cut (as opposed to a bikini cut) integral disposable diaper having elastically contractable side portions (i.e., elasticized leg-cuffs) and tape-type fasteners.

While some of the problems of providing low cost waste-containment garments have been at least partially ameliorated by garments of the types disclosed in the background patents, none has solved the problems to the same extent in the same manner as the present invention. That is, by providing a bikini-shape disposable absorbent body member having a narrow absorbent core (i.e., loin-cloth shape) and elasticized leg-cuffs which absorbent body member is secured on a wearer through the use of inelastic, reuseable side-bridging fastener fitments: preferably fastener fitments which comprise means for obviating roping as well as substantially obviating marking the skin of the wearer; which comprise means for enabling one-handed application; and which are sufficiently small to be wholly disposed in the side-waist regions of a wearer whereby soiling and or wetting thereof is substantially obviated.

DISCLOSURE OF THE INVENTION

In accordance with one aspect of the present invention, a waste-containment garment is provided which comprises an absorbent body having elasticized leg-cuffs, and side-bridging fastener fitments. The absorbent body is sufficiently narrow in its waist-band regions to obviate overlapping back and front corners. Upon applying the garment to a wearer through the use of the side-bridging fastener fitments, the leg-cuffs of the absorbent body are sufficiently stretched to sealingly engage them with skin surfaces of the wearer: preferably inwardly facing upper thigh areas of the wearer but which may include outwardly facing upper thigh areas and/or abdominal areas and/or hip areas of the wearer. Preferably, the absorbent body comprises a narrow absorbent core, a liquid impervious backsheet, and elasticized longitudinally extending leg cuffs disposed adjacent longitudinally extending side edges of the core. Such an absorbent body may be rectangular or hour-glass shape; and may include grommets on its corners to facilitate securing it on a wearer through the use of snap-type fastener fitments or the like. Additionally, the side-bridging fastener fitments are preferably hinged assemblies which are sufficiently rigid to enable one-hand fastening; have sufficient transverse rigidity to obviate roping; and have sufficiently flexible longitudinal edges to substantially obviate their marking the skin of the wearer.

BRIEF DESCRIPTION OF THE DRAWINGS

While the specification concludes with claims particularly pointing out and distinctly claiming the subject matter regarded as forming the present invention, it is believed the invention will be better understood from the following descriptions taken in conjunction with the accompanying drawings in which:

FIG. 5 is a plan view of a side-bridging snap-type fastener fitment such as shown in FIG. 1 and in which plan view one end portion is turned back to disclose underlying structure.

FIG. 6 is an exploded sectional view taken along line 6—6 of FIG. 5.

FIG. 7 is a view of an alternate embodiment side-bridging fastener fitment.

DETAILED DESCRIPTION OF THE INVENTION

Figure 1:
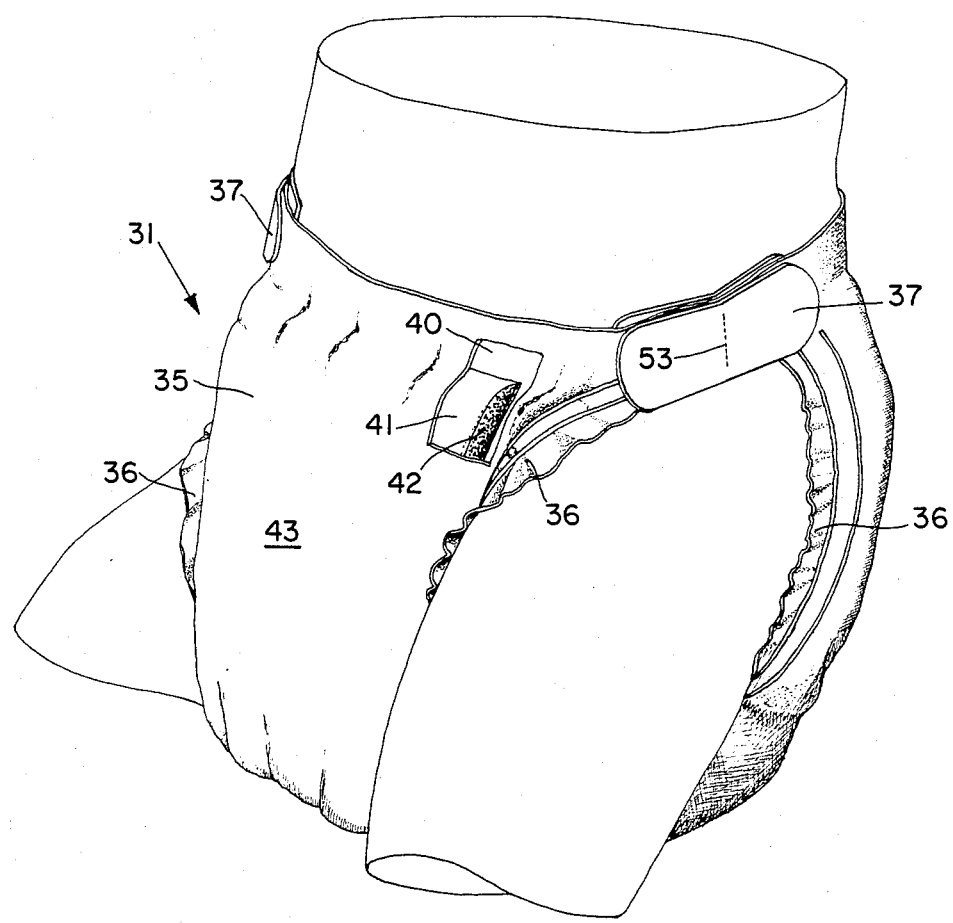
FIG. 1 is a perspective view of an exemplary, waste-containment garment embodiment of the present invention which has been secured on a fragmentary portion of a manikin.

An exemplary embodiment of the present invention is shown in FIG. 1 to be a waste-containment garment 31 which comprises an absorbent body 35 having elasticized leg-cuffs 36, and two side-bridging fastener fitments 37. Additionally, as shown in FIG. 1, the absorbent body 35 comprises a topsheet 40, a narrow absorbent core 41 having side edges 42, and a backsheet 43.

Briefly, the present invention provides an economical waste-containment garment which preferably comprises a disposable body or chassis assembly and two fastener fitments for securing the chassis on a wearer. As shown in the exemplary embodiment of FIG. 1, the chassis is bikini cut (i.e., low in the front and the back) and has a relatively lightweight, narrow, and short absorbent core disposed between a liquid permeable topsheet and a liquid impervious backsheet. The absorbent core is said to be loin-cloth shaped due to its limited size: i.e., due to the limited area it is sized to cover. Portions of the chassis which extend adjacent the longitudinal edges of the absorbent core are elasticized: i.e., are elasticized leg-cuffs. The chassis is secured on a wearer by relatively short, inelastic side-bridging fastener fitments which, due to the bikini-cut of the chassis, are disposed across the side portions of the wearer's hip bones just above the thigh-torso junctures of the wearer rather than being entirely disposed superior to the side portions of the wearer's hip bones.

Figure 2:
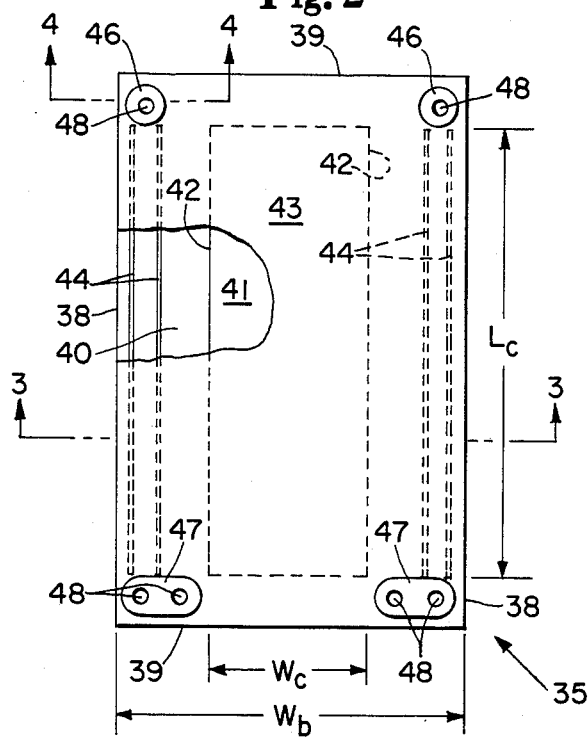
FIG. 2 is a plan view of the absorbent body of the waste-containment garment shown in FIG. 1, and which plan view is taken looking at the outwardly facing surface of the backsheet of the body with the body in a non-contracted state: i.e., flat out rather than being contracted by strands of elastic which are disposed in its leg cuff areas.

Referring now to FIG. 2, absorbent body 35 of garment 31, FIG. 1, is shown in its flat-out state with all elastic induced contraction pulled out. The backsheet 43 faces upward and a portion thereof is torn away to reveal the underlying structure. Absorbent body 35 is shown in FIG. 2 to comprise a topsheet 40, absorbent core 41 having longitudinal edges 42, backsheet 43, and elastic strands 44. The portions of the topsheet and backsheet which extend laterally from the side edges 42 of core 41 are secured together as by adhesive (not shown) and, due to their inherent flexibility and the elasticity of strands 44, are designated elasticized leg-cuffs 36, FIG. 1.

An exemplary absorbent body 35 was constructed in which the backsheet 43 is a matte-finish polyethylene film having a nominal thickness of about one mil (about 0.0254 mm), and overall length and width of about fifteen inches by about eight inches, respectively (about 38.1 by 20.3 cm, respectively); the topsheet 40 is a nonwoven polypropylene having a nominal thickness of about three to five mils (about 0.056 mm to about 0.127 mm), and length and width about equal to the corresponding dimensions of the backsheet; an air laid fibrous core 41 having a nominal weight of about 30.7 grams, a nominal caliper of about 7.1 mm, and length and width of about thirteen by four inches, respectively (about 33 by 10.2 cm, respectively); strands 44 of elastic having nominal unstretched thickness and width of about 0.2 and 2.4 mm, respectively, and which had been stretched about one-hundred-twenty-five percent (125%) prior to being adhesively secured to the backsheet, and prior to adhesively securing the topsheet to the backsheet whereby the longitudinal side edges of the absorbent body (i.e., the elasticized leg-cuffs 36) have nominal extensions (i.e., their available stretch as a percent of their elastically contracted length) of about forty-five percent or greater. Additionally, the core is enveloped with a low basis weight tissue paper (not shown) to provide structural integrity. As also shown in FIG. 2, one-hole grommets 46 are affixed to each back corner of backsheet 43, and a two-hole grommet 47 is affixed to each front corner of backsheet 43. The grommets 46 and 47 are described more fully below in conjunction with describing FIG. 4.

As further shown in FIG. 2, the elastic strands 44 extend longitudinally between the grommets 46 and 47, and the strands 44 are disposed adjacent the longitudinal side edges 38 of the absorbent body. In the exemplary absorbent body, the inboard edge of the elastic strand 44 disposed closest to the absorbent core 41 is spaced therefrom about one-and-seven eighths inches (about 4.76 cm). Accordingly, the elasticized leg-cuffs 36—being relatively wide—can be contracted and stretched without having to induce crumpling or longitudinal compression of the core. Thus, stretching induced tension is available for sealingly engaging the leg-cuffs 36 with skin areas of a wearer rather than being vitiated by trying to longitudinally compress the core. FIG. 2 also shows that portions of the grommets 46 and 47 are disposed in longitudinal alignment with the elastic strands 44, and that the grommets are longitudinally spaced a distance Lc apart: i.e., the length of core 41. In the exemplary absorbent body Lc is about thirteen inches (about 33 cm).

Figure 3:
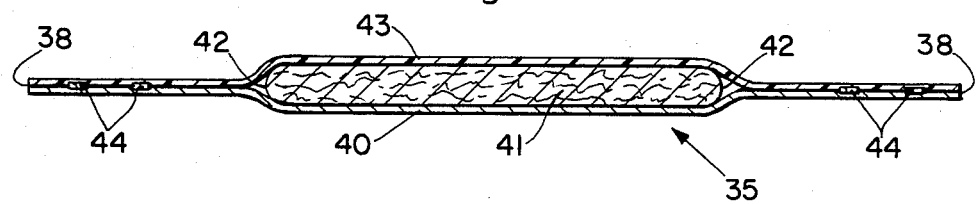
FIG. 3 is a fragmentary sectional view taken along line 3—3 of FIG. 2.

FIG. 3 is a transverse sectional view taken along line 3—3 through absorbent body 35, FIG. 2. As shown in FIG. 2, the backsheet 43 and topsheet 40 of absorbent body 35 are joined together along the longitudinal side edges 42 of absorbent core 41, and coextensively extend outwardly therefrom. Elastic strands 44 are secured intermediate topsheet 40 and backsheet 43 adjacent the longitudinal side edges 42 of absorbent body 35. Thus, the laminated regions of the backsheet and topsheet disposed outboard of core edges 42 are generally referred to as elasticized leg-cuffs due to the pliability of the topsheet and the backsheet in combination with the elasticity of the elastic strands 44. However, the most effective portion of these cuffs with respect to liquid sealing is the portion disposed immediately adjacent the elastic strands. Thus, lines of tension induced sealing are principally disposed—when the absorbent body is applied to a wearer as described hereinbefore—intermediate the outer surface of topsheet 40 and the skin of the wearer in the zones disposed between the pairs of elastic strands: one line or band of sealing for each pair of elastic strands. However, it is not thereby intended to limit the present invention to this particular elasticized leg-cuff construction. Rather, for example, elasticized films or other elastically contractible material may be used rather than strands of elastic. Alternatively, of course, only one strand of elastic per leg-cuff may be used to achieve substantial waste containment.

Figure 4:
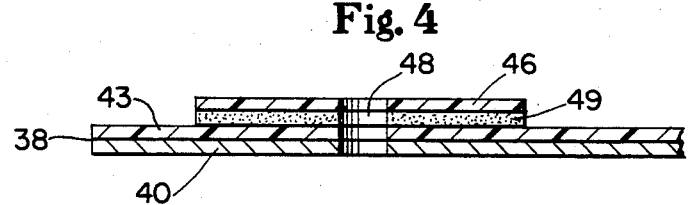
FIG. 4 is a fragmentary sectional view taken along line 4—4 of FIG. 2.

FIG. 4 is a fragmentary sectional view taken along line 4—4 of FIG. 2. This shows a one-hole grommet 46 secured to a back corner area of the backsheet 43 by adhesive 49; and shows that the hole designated 48 extends through the entire assembly although it is not intended to thereby limit the present invention. Such grommets may be made from Mylar (registered TM of DuPont) or other tape having adequate strength to sufficiently reinforce the corners of the absorbent body to survive the stresses imposed by snap fasteners and the like.

Referring now to FIG. 5, an exemplary side-bridging fastener fitment 37 is shown to comprise a top panel 51 and a bottom panel 52 which are oblong-shape and which are sewn together along a line of stitching 53. Thus, due to the materials of construction which are further described below, fastener fitment 37 comprises four panels which are commonly hinged by the line of stitching: the four panels comprising the left and right halves of both the top panel 51 and the bottom panel 52. Both the left and right halves of top panel 51 have a male-half 58 of a snap-fastener sewn to it with stitches 60; and both the left and right halves of bottom panel 52 have a female-half 59 of a snap-fastener sewn to it with additional stitches 60. As described more fully below, fitment 37 is so constructed that its panels may be manipulated with one hand of a user to fasten the right halves of panels 51 and 52 together so that the post of the male-half snap-fastener 58 extends through a hole 48 in a grommet 46 or 47, FIG. 2, and snaps into the female-half snap-fastener 59. In the same manner, the left halves of panels 51 and 52 are manipulated to complete the installation of a fastener fitment 37 on an absorbent body 35 so that the fitment bridges a side portion of a wearer as shown in FIG. 1. Additionally, fastener fitment 37 is so constructed that it has sufficient transverse rigidity to obviate roping; and has sufficiently flexible longitudinal edge portions that their marking the skin of the wearer is substantially obviated. This construction is described below.

FIG. 6 is an exploded section view of fastener fitment 37 taken along section line 6—6 of FIG. 5. This is an exemplary construction for achieving sufficient transverse rigidity to obviate roping as stated above; and to provide sufficiently flexible or compliant longitudinal edges to substantially obviate their marking the skin of a wearer as also stated above.

In FIG. 6, both top panel 51 and bottom panel 52 of fastener fitment are shown to comprise outer plies 71, and interior plies 73 which are laminated together with layers of adhesive 72 and 74. The halves 58 and 59 of the snap-fasteners are sewn with stitches 60 to subassemblies comprising one outer ply 71, and one interior ply 73 adhesively secured together with a layer of adhesive 74 prior to completing the assembly of panels 51 and 52. The edges of the interior plies are designated 56 in FIGS. 5 and 6. Thus, the transverse rigidity of fastener fitment 37 across the width of the interior plies 73 is derived from all of the plies; and the rigidity/flexibility of the longitudinal edge portions of the fitments 37 (i.e., the portions along the long sides of fitment 37 disposed outboard of edge 56) is derived from only the two outer plies 71 which are secured together with adhesive 72, FIG. 6. In such assemblies, the materials can be selected to provide the combination of transverse rigidity and edge flexibility described above: i.e., sufficient transverse rigidity to obviate roping (causing it to roll up into a rope-like body when subjected to longitudinal stress which roping would precipitate wearer discomfort); and sufficient longitudinal flexibility to substantially obviate red-marking the skin of the wearer.

An exemplary fastener fitment of the configuration shown and described as fitment 37 was constructed as follows. The outer plies 71 were made from Sontara (registered TM of DuPont) style 8103 having a weight of about sixty-eight grams/square meter; and overall length and width of about 6.7 cm by about 3.2 cm, respectively. Sontara is a spunlaced fabric of one-hundred percent polyester fibers and has a flannel appearance. The interior plies 73 were Shirtailor Pellon (registered TM of Pellon Corporation, New York, N.Y.) which is a non-woven fusible interfacing having adhesive 74 applied thereto to make it fusible. The Pellon weighed 12.5 grams per square foot or about 135 grams per square meter. The layers of adhesive 72 were Stitch Witchery which is a fusible material for joining fabrics without stitching and weighed about 3.9 grams per square foot or about 42 grams per square meter; and was obtained from Stacy Fabric Corp., Wood-Ridge, N.J. The male and female snap fasteners were size 4, style 511 manufactured by William Pryme, Inc., Dayville, Conn.

Garment 31, FIG. 1, is preferably secured on a wearer by applying the side-bridging fitments as shown in FIG. 1 after stretching the absorbent body (i.e., its elasticized leg-cuffs 36) and dressing the leg-cuffs 36 as generally shown. Due to the bikini cut of absorbent body 35, the cuff lines generally lie along the outboard regions of the fleshy portions of the wearer's hips, and angle upward and outward from the crotch region across the abdominal area of the wearer. Thus, the leg-cuffs 36 do not encircle the thighs per se, it having been discovered that circular-shape lines of sealing are not required to achieve satisfactory waste containment.

While the exemplary embodiment of garment 31 has been described and shown to have a rectangular-shape absorbent body 35 and a rectangular-shape absorbent core 41, either or both could have reduced width crotch regions. Also, whereas absorbent body 35 has elastic strands which extend the full length of the absorbent core 41, they could be shortened to the regions adjacent the crotch region.

ALTERNATE EMBODIMENT FASTENER-FITMENT

FIG. 7 shows an alternate embodiment fastener fitment designated 137. The elements or features of fitment 137 which are identical to those of fitment 37 are identically designated: e.g., snap fastener halves 58 and 59. The elements or features of fitment 137 which correspond to but are not identical to counterparts in fitment 37 are identified by designators having the same tens and units digits, and increased by one hundred; e.g., edges 156 of the interior plies of fitment 137 vs. edges 56 of the interior plies of fitment 37. As shown, fitment 137 comprises one pair of panels which are hinged together along line 153. This would be applied so that the hinge line would be generally aligned with the end edges of the absorbent body 35, FIG. 1, as opposed to the hinge line 53 of fitment 37 being generally perpendicular to the end edges of absorbent body 35 as shown in FIG. 1. As indicated by the dotted lines 156, fitment 137 comprises interior plies which are smaller than the outer plies. This enables the fitment to be sufficiently inflexible to obviate roping and to enable one-hand closure, yet have sufficiently compliant edges to substantially obviate marking the skin of the wearer.

While fitments 37 and 137 have been described as composite laminates having snap fastener members sewn to them, it is not intended to thereby limit the present invention to either such composite structures or to snap-type fasteners per se. Rather, by way of example and not by way of limitation, side-bridging fastener fitments may comprise unitary molded constructions; fused rather than sewn assemblies; loop and post fasteners as commonly used on garters; or hook and eye type fasteners; or pinch-type fasteners as commonly used on suspenders.

While particular embodiments of the present invention have been illustrated and described, it would be obvious to those skilled in the art that various other changes and modifications can be made without departing from the spirit and scope of the invention. It is intended to cover in the appended claims all such changes and modifications that are within the scope of this invention.

What is claimed is:

1. A waste containment garment, said garment comprising an absorbent pad assembly and two discrete side-bridging fastener fitments, said absorbent pad assembly comprising a liquid pervious topsheet, a liquid impervious backsheet, an absorbent core disposed between said topsheet and said backsheet and elasticized leg cuffs, said pad assembly having front and back waistband regions having widths which total less than the midsection girth of an intended wearer of said garment, and said core having end regions having individual widths of from about fifteen to about thirty-five percent of the midsection girth of said wearer; and each of said side-bridging fastener fitments comprising means for detachably securing one end of said fitment to a back corner of said pad assembly and for detachably securing the other end of said fitment to the front corner of said pad assembly on the same side of said pad assembly as said back corner whereby each said fitment will bridge across a side portion of said wearer of said garment said side-bridging fasteners further comprising means for being substantially inelastic longitudinally, for having sufficient transverse rigidity to obviate roping, and for having sufficiently compliant longitudinal edge regions to substantially obviate edge marking the skin of said wearer.

2. The waste containment garment of claim 1 wherein said side-bridging fasteners comprise complimentarily configured fastening means, and a plurality of hinged panels, said fastening means being configured and disposed to engage when said hinged panels are pressed together with a said corner of said pad assembly interposed therebetween.

3. The waste containment garment of claim 2 wherein said hinged panels have sufficient rigidity to enable thumb-and-forefinger engagement of said fastening means.

4. The waste containment garment of claim 1 wherein said absorbent pad assembly further comprises a reinforcing member secured to each of its corners.

5. The waste containment garment of claim 4 wherein said reinforcing members are perforated with a hole to enable engaging fastening members therethrough.

6. The waste containment garment of claim 5 wherein each said reinforcing member has a plurality of said holes which are so disposed to enable fitting said garment to a range of wearer sizes.

7. The waste containment garment of claim 5 or 6 wherein said holes extend completely through said corners.

8. A double-ended fastener fitment which is adapted to bridge between a front corner and a back corner of an absorbent pad of a waste-containment garment when said garment is applied to a wearer, said fastener fitment comprising two pairs of hinged panels which pairs extend oppositely from their hinged proximal ends, and complimentarily configured fastening means disposed on distal portions of said hinged panels, said hinged panels being sufficiently rigid and said fastening means being so configured and disposed to enable one-hand fastening of each of said pairs of hinged panels to a corner of said waste-containment garment means when said hinged panels are pressed together said fastener fitment further comprising means having sufficient transverse rigidity to obviate roping and sufficiently compliant longitudinal edge regions to substantially obviate edge marking the skin of said wearer.

* * * * *